(12) United States Patent
Rottenberg et al.

(10) Patent No.: US 10,206,588 B2
(45) Date of Patent: Feb. 19, 2019

(54) DEVICE AND SYSTEM FOR SENSING WITHIN IN-VIVO FLUIDS

(71) Applicant: GIVEN IMAGING LTD., Yoqneam (IL)

(72) Inventors: Dan Rottenberg, Haifa (IL); Robert Sayegh, Haifa (IL)

(73) Assignee: GIVEN IMAGING LTD., Yoqneam (IL)

( * ) Notice: Subject to any disclaimer, the term of this patent is extended or adjusted under 35 U.S.C. 154(b) by 921 days.

(21) Appl. No.: 14/212,304

(22) Filed: Mar. 14, 2014

(65) Prior Publication Data

US 2014/0275860 A1  Sep. 18, 2014

Related U.S. Application Data

(60) Provisional application No. 61/789,105, filed on Mar. 15, 2013.

(51) Int. Cl.
| | |
|---|---|
| *A61B 5/00* | (2006.01) |
| *A61B 5/02* | (2006.01) |
| *A61B 5/07* | (2006.01) |
| *A61B 1/04* | (2006.01) |
| *A61B 1/06* | (2006.01) |
| *A61B 1/00* | (2006.01) |

(52) U.S. Cl.
CPC ...... *A61B 5/02042* (2013.01); *A61B 1/00087* (2013.01); *A61B 1/041* (2013.01); *A61B 1/06* (2013.01); *A61B 5/0084* (2013.01); *A61B 5/073* (2013.01); *A61B 5/4233* (2013.01); *A61B 5/4238* (2013.01); *A61B 5/4255* (2013.01); *A61B 2562/162* (2013.01); *A61B 2562/18* (2013.01)

(58) Field of Classification Search
CPC ....... A61B 1/041; A61B 5/073; A61B 5/0084; A61B 5/1459; A61B 2562/0238; A61B 5/6861; A61B 2562/162; A61B 5/4233; A61B 5/4238; A61B 5/4255
See application file for complete search history.

(56) References Cited

U.S. PATENT DOCUMENTS

| | | |
|---|---|---|
| 6,632,171 B2 | 10/2003 | Iddan et al. |
| 6,884,213 B2 | 4/2005 | Raz et al. |

(Continued)

FOREIGN PATENT DOCUMENTS

WO  WO 2010/086859  8/2010

*Primary Examiner* — Christian Jang
*Assistant Examiner* — Karen Toth
(74) *Attorney, Agent, or Firm* — Pearl Cohen Zedek Latzer Baratz LLP (57) ABSTRACT

Devices and a system for detection of blood within in-vivo fluids are provided. A device comprises a housing that includes a gap. The gap has at least one opening through which in-vivo fluids may enter and/or exit the gap. The device further comprises an illumination source for illuminating the in-vivo fluids in the gap, a light detector for detecting light which passes through the in-vivo fluids in the gap, and flexible fins disposed on the housing in the vicinity of the gap's opening for covering the opening when the fins are folded and for pumping fluids into and out of the opening by repeated closure and opening of the opening by the fins, due to repeated peristaltic waves. This pumping effect may lead to continuous flow of fluids into and out of the opening and thus into and out of the gap of the device.

9 Claims, 6 Drawing Sheets

(56) References Cited

U.S. PATENT DOCUMENTS

| | | | |
|---|---|---|---|
| 2008/0208077 A1* | 8/2008 | Iddan | A61B 1/041 600/582 |
| 2009/0264697 A1* | 10/2009 | Tovar Lopez | A61M 1/106 600/16 |
| 2011/0306855 A1* | 12/2011 | Rabinovitz | A61B 5/0084 600/310 |

* cited by examiner

DEVICE AND SYSTEM FOR SENSING WITHIN IN-VIVO FLUIDS

CROSS-REFERENCE TO RELATED APPLICAITONS

This application claims priority from U.S. Provisional Patent Application No. 61/789,105, filed Mar. 15, 2013, which is incorporated herein by reference.

FIELD OF THE INVENTION

The present invention relates to the field of in-vivo sensing and detection. More specifically the present invention relates to devices and systems for in-vivo detection of blood in the gastrointestinal (GI) tract.

BACKGROUND OF THE INVENTION

In-vivo bleeding may occur due to different diseases in the body. Bleeding in the gastrointestinal (GI) tract may occur in various locations along the GI tract, and this may indicate different pathologies present at those locations. For example, bleeding in the esophagus may be due to esophagitis or due to ruptures in varices in the esophagus. An ulcer in the stomach, as well as an ulcer in the duodenum, may cause bleeding. And, in the lower digestive tract, colorectal cancer may cause occult bleeding. Therefore, early detection of bleeding along the GI tract may be crucial for better treatment of many patients.

An in-vivo device that may be used to detect in-vivo bleeding is described in International Patent Application Publication No. WO 2010/086859. For example, as shown in FIGS. 1A-1B of International Patent Application Publication No. WO 2010/086859, such an in-vivo device comprises a housing having a gap, through which in-vivo fluids may enter and exit. On one side of the gap is at least one illumination source, and on the other side of the gap, facing the illumination source, is a light detector. The illumination source may illuminate the in-vivo fluids which freely flow through the gap, and the light passing through the fluids may then be detected by the light detector. Following experiments with such a device, it was realized that tissue and bubbles occasionally enter the gap and either stay inside the gap or block the gap for substantial periods of time. When tissue and/or bubbles are stuck inside the gap such that they are positioned between the illumination source and the light detector, readings by the light detector are disrupted, and thus true indication of presence of blood within in-vivo fluids is not possible.

There is, therefore, a need to add to such in-vivo devices (as the device described in International Patent Application Publication No. WO 2010/086859) new means in order to prevent tissue and/or bubbles from entering the gap between the illumination source and the light detector, while enabling free flow of in-vivo fluids in and out of the gap. Such new means may ensure accurate and reliable readings of the light that passes through the in-vivo fluids, which freely flow in and out of the gap, without any disruption by tissue and/or bubbles.

SUMMARY OF THE INVENTION

Devices and systems according to the present invention comprise protective means that on one hand prevent entry of tissue into the device, and on the other hand allow continuous flow of in-vivo fluids into and out of the device, which also allows bubbles that are trapped within the device to exit out of the device within short periods of time. The protective means of the present invention may comprise elements that push tissue away from the opening of the device. These protective means may further comprise wide enough openings through which in-vivo fluids may flow into and out of the openings, and thus into and out of the device. And yet further, these protective means may comprise a mechanism that allows frequent evacuation of fluids and bubbles from the device. Such protective means may provide a device that performs reliable and accurate readings of in-vivo fluids' characteristics, since substantially no interruptions take place during operation of the device.

According to embodiments of the invention, an in-vivo sensing device for detection of blood within in-vivo fluids comprises a housing. The housing comprises a gap having at least one opening through which in-vivo fluids may enter and/or exit the gap. The housing may further comprise an illumination source for illuminating the in-vivo fluids in the gap, and a light detector for detecting light which passes through the in-vivo fluids in the gap. The housing may further comprise flexible fins disposed on the housing in the vicinity of the opening for covering the opening when the fins are folded.

In some embodiments of the invention, the in-vivo sensing device may comprise flexible scales instead of flexible fins. The flexible scales may be positioned around the circumference of the housing of the device.

According to some embodiments of the invention the device further comprises a second gap through which in-vivo fluids may enter and/or exit, an illumination source for illuminating the in-vivo fluids in the second gap, and a light detector for detecting light which passes through the in-vivo fluids in the second gap. The device may further comprise a membrane covering the second gap. In some embodiments, the membrane enables passage of particles of a certain size into and/or out of the gap. In some embodiments, the second gap, illumination source and light detector covered by the membrane are located on one end of the device's housing, opposite the end comprising the opening covered by the fins.

In some embodiments, the in-vivo device may comprise two sensing heads comprising different protective means on each end of the housing. In some embodiments, the device may comprise flexible fins or flexible scales as protective means on a first end of the housing, while on the second end of the housing the protective means may be a membrane. The flexible fins or flexible scales may be a protective mean suitable for the small bowel, and the membrane may be a protective mean suitable for the colon.

According to some embodiments, an in-vivo sensing system for detection of blood within in-vivo fluids comprises an in-vivo sensing device that comprises a housing. In some embodiments, the housing comprises a gap having at least one opening through which in-vivo fluids may enter and/or exit the gap, an illumination source for illuminating the in-vivo fluids in the gap, and a light detector for detecting light which passes through the in-vivo fluids in the gap. In some embodiments, the housing may further comprise flexible fins disposed on the housing in the vicinity of the opening for covering the opening when the fins are folded. In some embodiments, the device may comprise a transmitter for transmitting signals detected by the light detector. According to some embodiments, the system may further comprise a receiver for receiving the detected signals, and a processing unit for processing the detected signals to determine presence of blood in-vivo.

In some embodiments, the device further comprises an illumination source for illuminating broad band illumination, and an imager for acquiring in-vivo images. In some embodiments, the broad band illumination source and the imager are positioned on one end of the device's housing opposite the end comprising the illumination sources, the gap and the light detector.

In some embodiments, the in-vivo device is a swallowable capsule.

BRIEF DESCRIPTION OF THE DRAWINGS

The present invention will be understood and appreciated more fully from the following detailed description taken in conjunction with the appended drawings in which.

It will be appreciated that, for simplicity and clarity of illustration, elements shown in the figures have not necessarily been drawn accurately or to scale. For example, the dimensions of some of the elements may be exaggerated relative to other elements for clarity, or several physical components may be included in one functional block or element. Further, where considered appropriate, reference numerals may be repeated among the figures to indicate corresponding or analogous elements.

DETAILED DESCRIPTION OF THE INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as to not obscure the present invention.

Figure 1:
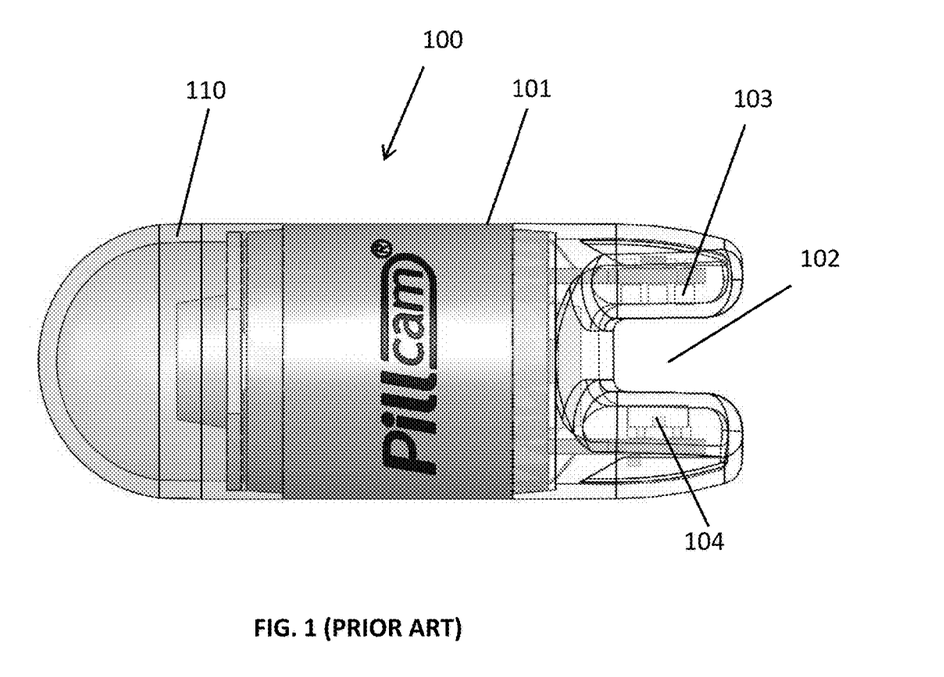
FIG. 1 is a schematic illustration of a side-view of an in-vivo device for the detection of blood within in-vivo fluids in accordance with the prior art.

Reference is now made to FIG. 1, which provides a schematic illustration of a side-view of an in-vivo device for the detection of blood within in-vivo fluids in accordance with the prior art. Device 100, as described in International Patent Application Publication No. WO 2010/086859, is typically autonomous, and is typically self-contained. For example, device 100 may be a capsule or other unit where all the components including, for example, power components, are substantially contained within a housing or shell 101, and where device 100 does not require any wires or cables to, for example, receive power or transmit information. Device 100 may communicate with an external receiving and display system to provide display of data, control, or other functions. For example, in an autonomous system, power may be provided by an internal battery or a wireless receiving system. Other embodiments may have other configurations and capabilities. Device 100 may be made of a biocompatible material such as polycarbonate, e.g., Isoplast® and Makrolon®. Other biocompatible materials may be used.

Device 100 comprises device body 101 in which gap 102 is formed into or through. Gap 102 may be hydro-dynamically curved to allow continuous flow of in-vivo fluids in and out of gap 102. In some embodiments, the width of gap 102 may be between 4-5 mm, although other widths may be used. In order for gap 102 to allow continuous flow of fluids in and out of it, the device 100 should constantly be in contact with in-vivo fluids. Therefore, in some embodiments, device 100 has a specific gravity of just above 1. When the specific gravity of device 100 is above 1, device 100 may pass through the colon in an optimal way. Specific gravity of just above 1 may ensure, on one hand, that device 100 does not float above the fluids, i.e., that device 100 and, more specifically, gap 102 is in contact with the fluids, and, on the other hand, may ensure that device 100 does not sink to the bottom of the lumen wall and lose the ability to move freely.

On one side of gap 102 there may be an illumination source 103, such as an LED or a Vertical-cavity surface-emitting laser (VCSEL), and on the opposite side of the gap 102 there may be a light detector or photo detector 104. Illumination source 103 may be an LED such as Hyper TOPLED® by Osram™ and KPHHS-1005SYCK® by Kingbright™, though other illumination sources may be used. Light detector or photodiode 104 may be, for example, opt101® by Burr-Brown Products™ from Texas Instruments, mlx75305C® by Melexis™ Microelectronic Integrated Systems, or tsl12s-e23® by TAOS™ (Texas Advanced Optoelectronic Solutions). Other photodiodes may be used. Light detector 104 is positioned such that it is directly facing the illumination source 103, while gap 102 is located between illumination source 103 and light or photo detector 104. Illumination source 103 may illuminate the in-vivo fluids which freely flow through gap 102, and the light passing through the fluids (whether some of the light was absorbed by particles in the fluid, or whether some of it was reflected from the flowing particles) may then be detected by light detector 104. According to some embodiments, the illumination source 103 may illuminate at a low frequency in order to save energy during the procedure of blood detection. Detector 104 may also be activated in synchronization with the illumination source 103, e.g., illumination source 103 and light detector 104 may detect signals every 10 sec or every 1 minute. Other frequencies may be used.

While or after device 100 passes through the GI tract, the signals detected by light detector 104 are transmitted by a transmitter (not shown) to an external receiver (not shown), outside the patient's body. The receiver may include a processor, which may create transmission spectra of the in-vivo fluids according to the signals detected from illumination source 103. The processor may further compare the transmission spectra of the in-vivo fluids to a reference transmission spectra of bile and to a reference transmission spectra of blood, which are created by detecting transmission spectra of bile and of blood in water and of different concentrations of bile vs. blood, and thus determine whether there is bile in-vivo, whether there is blood in-vivo or whether there are both.

Device 100 may comprise an imaging head 110, which may comprise an optical system, illumination sources and an imager for acquiring images of the in-vivo environment through which device 100 passes along.

Device 100 may be a swallowable capsule. Typically, device 100 is inserted into the gastrointestinal (GI) tract of a patient by swallowing it. Other ways of insertion of device 100 may be used, e.g., by a capsule delivery device such as the one disclosed in U.S. Pat. Nos. 6,632,171 and 6,884,213, or by surgery. Device 100 may pass along the GI tract through natural peristalsis movements.

Following experiments with device 100 in humans and in animals, it was found that GI tissue and bubbles flowing within the in-vivo fluids of the GI tract tend to enter gap 102. Occasionally, the tissue and/or bubbles get stuck inside gap 102 for relatively long periods of time. This phenomenon causes false positive or illegal readings by light detector 104, since, instead of acquiring readings from light that passes through the in-vivo fluids, light detector 104 acquires readings of light passing through tissue or through bubbles. Device 100 should detect blood flowing as part of the in-vivo fluids, and tissue and/or bubbles disrupt continuous flow of fluids through gap 102 of device 100.

This problem of tissue and/or bubbles entering the gap is mainly a problem along the small bowel area of the GI tract. The tissue of the small bowel is soft and covered with villi that could enter even narrow gaps as in device 100, e.g., a gap of 4-5 mm. Furthermore, the small bowel is of a small diameter such that when a peristaltic wave passes along the small bowel, the small bowel tissue contracts and may squeeze on any content within it, such that if an in-vivo sensing device is present within the small bowel, during peristaltic waves the small bowel's tissue would be squeezed against the housing of the device. And if the in-vivo sensing device comprises a gap, the small bowel's tissue may enter the gap. Tissue entering the gap may interrupt operation of the sensor within the in-vivo sensing device, since, for example, tissue may provide false positive readings of presence of blood due to presence of blood vessels within the tissue.

Furthermore, bubbles typically present within in-vivo fluids flowing along the GI tract, mainly in the small bowel, may enter the gap of the in-vivo sensing device, and be trapped inside the gap for long periods of time if not for the entire procedure. Bubbles entering the gap may interrupt operation of the sensor located in the gap, since bubbles may provide false readings.

Flow of in-vivo fluids along the small bowel is quite fast compared to other areas of the GI tract (e.g., fluid flow in the small bowel is much faster than fluid flow in the colon). Therefore, it is most important to avoid interruptions and allow continuous flow of fluids through the device during readings of the sensor while the device is in the small bowel, so as to get as much information as possible from the in-vivo fluids flowing within the small bowel.

Therefore, new devices with new means to overcome such a problem are presented in this invention. These new devices are examples for devices with protective means that on one hand prevent entry of tissue into the device, and on the other hand allow continuous flow of in-vivo fluids into and out of the device, which also allows bubbles that are trapped within the device to exit out of the device within short periods of time. These protective means may comprise elements that push tissue away from the opening of the device. These protective means may further comprise wide enough openings through which in-vivo fluids may flow into and out of the openings, and thus into and out of the device. And yet further, these protective means may comprise a mechanism that allows frequent evacuation of fluids and bubbles from the device. Such protective means may provide a device that performs reliable and accurate readings of in-vivo fluids' characteristics, since substantially no interruptions take place during operation of the device.

A net having a dense grid, as protective means, might be too restrictive (depending on the size of its holes) since it may block not only the tissue but also the flow of fluids, and since it may be blocked by residue and content. A dense net may also not allow evacuation of bubbles that already entered the gap, which presence interrupts readings of the sensor within the in-vivo sensing device.

Figure 2A:
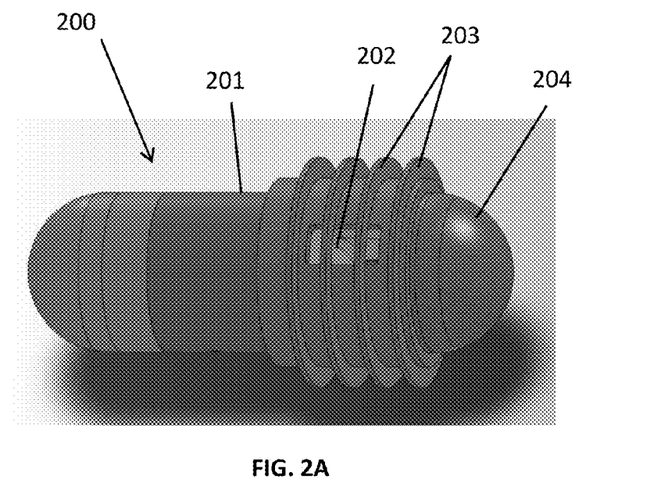
FIGS. 2A-2C are schematic illustrations of a side-view of an in-vivo device for the detection of blood within in-vivo fluids, a cross-section side-view of a section of the device and an external perspective view of the device, in accordance with a first embodiment of the invention, respectively.
Figure 2B:
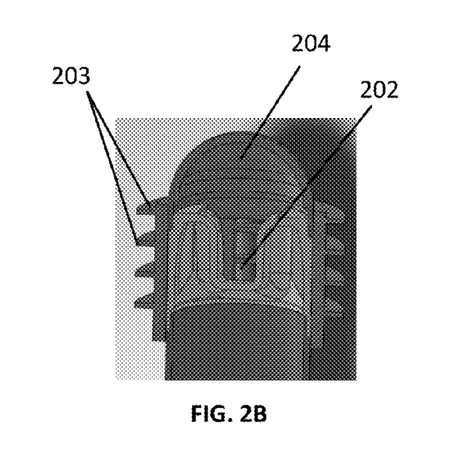
Figure 2C:
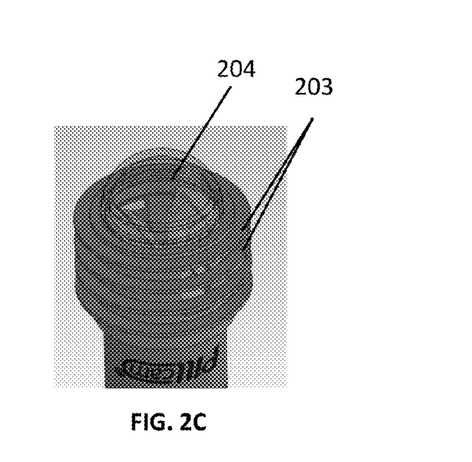

Reference is now made to FIGS. 2A-2B, which schematically illustrate a side-view of an in-vivo device for the detection of blood within in-vivo fluids, and a cross-section side-view of a section of the device, in accordance with a first embodiment of the invention, respectively. As shown in FIG. 2A, in-vivo device 200 may comprise housing or shell 201. In-vivo device 200 may be similar to device 100, i.e., device 200 may comprise an illumination source and a light detector on two sides of a gap. The gap may comprise at least one opening 202, such to enable continuous flow of in-vivo fluids into and out of the gap. Typically, the gap may comprise two openings, one across the other. However, in order to overcome the problem of tissue or mucosa, and/or bubbles, from entering and even getting stuck inside the gap, while enabling free flow of fluids into and out of the gap, device 200 may comprise means for keeping the tissue and bubbles away from the sensing area, i.e., the area between the illumination source and the light detector.

Housing 201 may comprise flexible fins 203 in the vicinity of, or adjacent to, opening 202. Flexible fins 203 may be in any shape, though typically circular so as to surround the entire circumference of housing 201 thereby surrounding opening 202. Flexible fins 203 are designed to fold when peristaltic pressure is applied onto them, and then to straighten again, i.e., unfold, once the pressure has been released. Peristaltic pressure, which causes the GI content (e.g., food) to move forward along the GI tract, also affects device 200 as it passes along the GI tract. Once peristaltic pressure is applied onto device 200, flexible fins 203 fold such to cover opening 202. As soon as the peristaltic pressure stops (e.g., when the peristaltic wave moves forward past device 200) flexible fins 203 may return to their straight (unfolded) position, e.g., their "rest state". The repeated closure and opening of opening 202 due to repeated peristaltic waves may mimic the operation of a pump. That is, the repeated closure and opening of opening 202 may lead to continuous flow of fluids into and out of opening 202, and thus into and out of the gap in device 200.

Flexible fins 203 may, on one hand, prevent the entrance of tissue or mucosa into device 200 through opening 202, since flexible fins 203 protrude from the circumference of housing 201 and may thus push the tissue away from opening 202, as well as block opening 202 once pressure is applied onto flexible fins 203. On the other hand, opening 202 is opened once peristaltic pressure ceases, thus in-vivo fluids may freely enter into opening 202 and thus into the gap. In the case where bubbles enter device 200 through opening 202, the 'pump-like' operation of flexible fins 203 may cause the bubbles to exit the gap through opening 202, thus clearing the sensing area between the illumination source and the light detector for reliable readings of light passing through in-vivo fluids (and not of tissue or bubbles).

Flexible fins 203 may be made of silicon, though other flexible biocompatible materials may be used, such as flexible elastomers, e.g., polyurethane. The number of flexible fins 203 may be selected by choice, according to the size of opening 202, such that they would cover and close opening 202 once folded due to applied pressure.

Housing 201 may further comprise cover 204 on the upper part of the gap, thus closing the top of the gap. Cover 204 may be part of housing 201 for the purpose of preventing tissue/bubbles from entering into the gap from the top area of the gap, besides the tissue/bubbles being blocked from the sides of the gap by flexible fins 203.

As shown in FIG. 2B, opening 202 may be encircled by flexible fins 203, and may further be covered from the top end by cover 204. Both flexible fins 203 and cover 204 prevent entrance of tissue and/or bubbles into opening 202, which is where fluids alone should enter to be examined for presence of blood. If bubbles did enter opening 202, they may exit through opening 202 due to the 'pump-like' operation of flexible fins 203 that fold or unfold, thus closing and opening the opening 202 when pressure is thereby applied or is ceased, respectively.

In some embodiments, flexible fins 203 and cover 204 may be part of a cover that is positioned over a gap through which in-vivo fluids may enter and/or exit device 200. That is, flexible fins 203 and cover 204 may be manufactured separately from device 200, and may be placed onto housing 201 so as to cover the gap and function as a barrier to tissue and/or bubbles entering device 200, while allowing continuous flow of in-vivo fluids in and out of device 200.

In some embodiments, device 200 may comprise an imaging head, which may comprise an optical system, illumination sources and an imager for acquiring images of the in-vivo environment through which device 200 passes along.

Figure 3A:
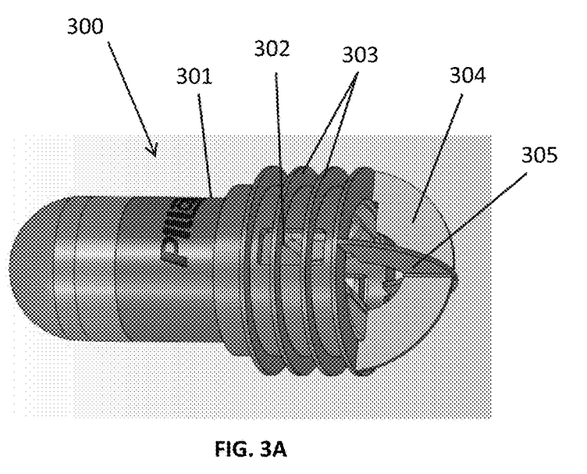
FIG. 3A is a schematic illustration of a side-view of an in-vivo device for the detection of blood within in-vivo fluids, in accordance with a second embodiment of the present invention.

Reference is now made to FIG. 3A, which schematically illustrates a side-view of an in-vivo device for the detection of blood within in-vivo fluids, in accordance with a second embodiment of the present invention. In-vivo device 300 may be similar to devices 100 and 200, such that detection of blood is performed by detecting light, which passes through in-vivo fluids that enter and exit through at least one opening of the device. Device 300 may comprise an illumination source, a light detector and a gap through which in-vivo fluids may freely pass. The gap, the illumination source, and the light detector may define a sensing area, in which readings of light, which will be used to determine presence of blood, are acquired. The gap may comprise at least one opening 302, such to enable continuous flow of in-vivo fluids into and out of the gap. Typically, the gap may comprise two openings one across the other. However, in order to overcome the problem of tissue or mucosa, and/or bubbles, from entering and even getting stuck inside the gap, while enabling free flow of fluids into and out of the gap, device 300 may comprise means for keeping the tissue and bubbles away from the sensing area, i.e., the area in between the illumination source and the light detector.

Device 300 may comprise housing or shell 301. Housing 301 may comprise flexible fins 303 in the vicinity of, or adjacent to, opening 302. Flexible fins 303 may be in any shape, though typically circular so as to surround the entire circumference of housing 301, thereby surrounding opening 302. Since housing 301 typically has a round finish in order to ease its administration to a patient, e.g., by swallowing it, flexible fins 303 may also have a round finish, e.g., flexible fins 303 may be in the shape of rings surrounding the perimeter of housing 301. Flexible fins 303 are designed to fold when pressure is applied onto them, and then to straighten again, i.e., unfold, once pressure is ceased. Peristaltic pressure, which causes the GI content (e.g., food) to move forward along the GI tract, also affects device 300, as it passes along the GI tract. Once peristaltic pressure is applied onto device 300, flexible fins 303 fold such to cover opening 302.

As soon as the peristaltic pressure stops (e.g., when the peristaltic wave moves forward past device 300) flexible fins 303 may return to their straight (unfolded) position, e.g., their "rest state". The repeated closure and opening of opening 302 due to repeated peristaltic waves may mimic the operation of a pump. That is, the repeated closure and opening of opening 302 may lead to continuous flow of fluids into and out of opening 302, and thus into and out of the gap in device 300.

Flexible fins 303 may on one hand prevent the entrance of tissue or mucosa into device 300 through opening 302, since flexible fins 303 protrude from the circumference of housing 301 and may thus push the tissue away from opening 302, as well as block opening 302 once pressure is applied onto flexible fins 303. On the other hand, opening 302 is opened once peristaltic pressure ceases, thus in-vivo fluids may freely enter into opening 302 and thus into the gap. In the case where bubbles enter device 300 through opening 302, the 'pump-like' operation of flexible fins 303 may cause the bubbles to exit the gap through opening 302, thus clearing the sensing area between the illumination source and the light detector for reliable readings of light passing through in-vivo fluids (and not of tissue or bubbles).

Flexible fins 303 may be made of silicon, though other flexible biocompatible materials may be used, such as flexible elastomers, e.g., polyurethane. The number of flexible fins 303 may be selected by choice, according to the size of opening 302, such that they would cover and close opening 302 once folded due to applied pressure.

Housing 301 may further comprise partitions 304 and 305, instead of cover 204 in device 200 (FIGS. 2A-2B). Walls or partitions 304 and 305 may be used instead of a full cover, and thus housing 301 may comprise more openings through which in-vivo fluids may enter and/or exit, so as to enable continuous flow of in-vivo fluids through device 300. Continuous flow of in-vivo fluids through device 300 is important for ensuring that readings of the light that passes through the fluids are readings of new fluids, and not repeated readings of fluids that were already examined. Walls or partitions 304 and 305 may be positioned over the top end of the gap in device 300. Partition 304 may be positioned at an angle with respect to partition 305, e.g., partition 304 may be perpendicular to partition 305 such that both partitions divide the top of the gap into four equal openings. In other embodiments, other positioning of one partition with respect to the other is possible.

The partitions may push tissue away from entering the top end of the gap, while keeping openings for fluids to enter and/or exit the gap. Furthermore, if bubbles happen to enter the gap, the pump-like operation of flexible fins 303 would cause the bubbles to exit through either of the openings of device 300, whether from the openings on the sides of the gap or from the openings on top of the gap, where partitions 304 and 305 are present. In some embodiments, only one partition or wall may be located at the top end of the gap in device 300, instead of two partitions 304 and 305, as illustrated in FIG. 3A.

Figure 3B:
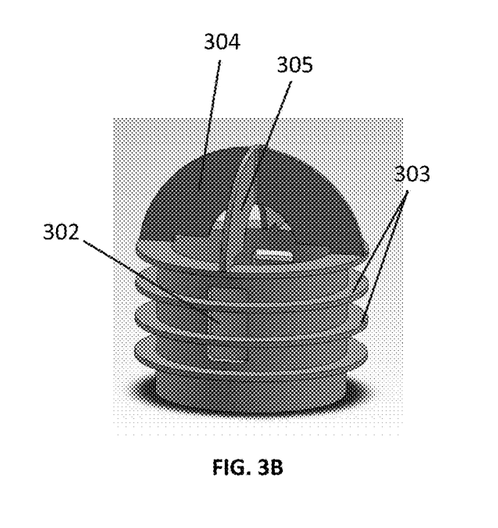
FIGS. 3B-3C are schematic illustrations of a side-view of a section of an in-vivo device and a prototype of an in-vivo device, in accordance with the second embodiment of the invention, respectively.

Reference is now made to FIG. 3B, which schematically illustrates a side-view of a section of an in-vivo device, in accordance with the second embodiment of the invention. According to some embodiments, flexible fins 303 and partitions 304 and 305 may be part of a cover that may be positioned over the gap through which in-vivo fluids enter and/or exit device 300. That is, flexible fins 303 and partitions 304 and 305 may be manufactured separately from device 300, and may be placed onto housing 301 so as to cover the gap and to function as a barrier to tissue and/or bubbles, while allowing continuous flow of in-vivo fluids in and out of device 300.

In some embodiments, device 300 may comprise an imaging head, which may comprise an optical system, illumination sources and an imager for acquiring images of the in-vivo environment through which device 300 passes along.

Device 300 may be administered into the GI tract, e.g., by swallowing. In some embodiments, device 300 may be a swallowable capsule.

Figure 3C:
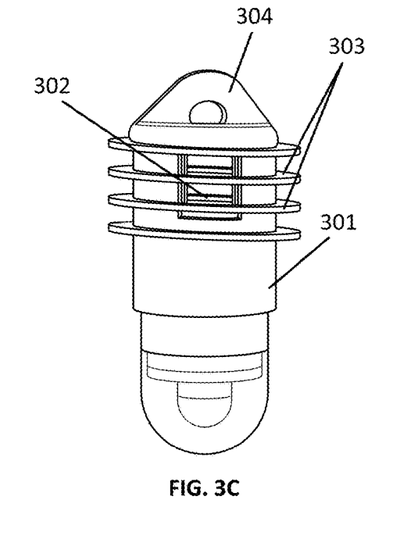

Reference is now made to FIG. 3C, which schematically illustrates a prototype of an in-vivo device, in accordance with the second embodiment of the invention. The prototype that was built according to the device in FIG. 3A comprises flexible fins 303 that when folded under pressure would cover opening 302. The prototype further comprises one wall or partition 304 located at the top end of the gap, thus preventing tissue from entering the gap from its top end, while keeping two openings to allow flow of fluids therethrough.

Figure 4A:
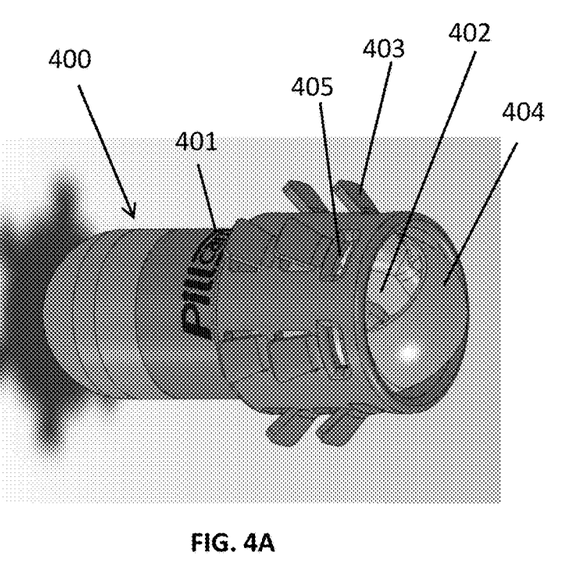
FIGS. 4A-4B are schematic illustrations of a side-view of an in-vivo device for the detection of blood within in-vivo fluids, and an upper-side-view of a section of the in-vivo device, in accordance with a third embodiment of the present invention, respectively.
Figure 4B:
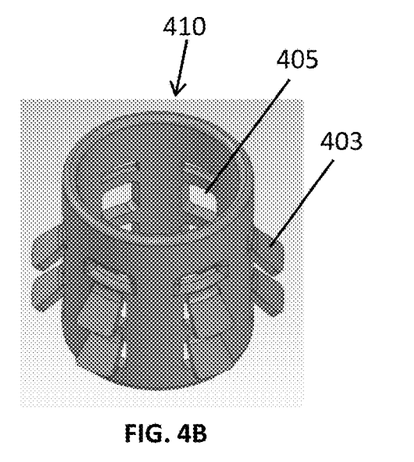

Reference is now made to FIGS. 4A-4B, which schematically illustrate a side-view of an in-vivo device for the detection of blood within in-vivo fluids, and an upper-side-view of a section of the in-vivo device, in accordance with a third embodiment of the present invention, respectively. According to FIG. 4A, device 400 may comprise housing 401. Device 400 may comprise an illumination source and a light detector on two sides of a gap. The gap may comprise at least one opening 402, so as to enable continuous flow of in-vivo fluids into and out of the gap. The illumination source illuminates the in-vivo fluids flowing through device 400, and the light detector detects light that passed through the in-vivo fluids. The readings acquired by the light detector are processed in order to determine presence of blood within the in-vivo fluids. In order to overcome the problem of tissue or mucosa, and/or bubbles from entering the gap, while enabling free flow of fluids into and out of the gap, device 400 may comprise means for keeping the tissue and bubbles away from the sensing area, i.e., the area in between the illumination source and the light detector.

In some embodiments, housing 401 may comprise a plurality of flexible scales 403 that may be positioned around the circumference of housing 401, adjacent to opening 402. Scales 403 may have rounded edges in order to avoid causing damage to the lumen walls while passing through the lumen. The number of scales may be determined by choice, according to the size of opening 402. Scales 403 may typically be made of flexible materials, e.g., silicone, though other flexible biocompatible materials may be used. The size of each scale may be determined so as to enable free flow of in-vivo fluids therethrough, while being small enough to prevent tissue from entering opening 402.

Device 400 may be administered into the GI tract, e.g., by swallowing. In some embodiments, device 400 may be a swallowable capsule.

Peristaltic pressure is what causes content within the GI tract to proceed forward along the tract. Before peristaltic pressure is applied onto housing 401, no pressure is applied onto scales 403, thus scales 403 are at rest, i.e., scales 403 are kept partially open so as to enable entrance and exit of in-vivo fluids through scales 403 into the sides of opening 402. However, when peristaltic pressure is applied onto housing 401, pressure is also applied onto scales 403, which causes scales 403 to fold and cover the sides of opening 402. Therefore, in the event of peristaltic wave passing along the GI tract, scales 403 are forced to close and cover the sides of opening 402 such that no fluids may enter or exit opening 402. Since peristaltic waves along the GI tract is a reoccurring phenomenon, the reopening and reclosing of scales 403 may mimic the operation of a pump. That is, peristaltic waves may cause in-vivo fluids to continuously flow through scales 403 and thus through opening 402, such that new fluids may constantly enter device 400 for determination of presence of blood within in-vivo fluids.

In some embodiments, housing 401 may further comprise openings 405. Openings 405 may be additional openings surrounding the circumference of device 400 that may enable further apertures through which in-vivo fluids may enter and/or exit the sensing area within the gap. Any number of openings 405 may be selected.

In some embodiments, device 400 may comprise a cover 404 for covering opening 402 from its top end. Cover 404 may be used to prevent entry of tissue into opening 402 and thus into the sensing area. Cover 404 may typically be a partial cover, in order to prevent entry of tissue into opening 402 while allowing entry of in-vivo fluids into opening 402 such to be examined for presence of blood.

In some embodiments, device 400 may comprise an imaging head, which may comprise an optical system, illumination sources and an imager for acquiring images of the in-vivo environment through which device 400 passes along.

According to FIG. 4B, scales 403 and openings 405 may be part of a component 410 separate from device 400, and which may be placed onto device 400 so as to keep tissue and bubbles away from the sensing area. That is, scales 403 and opening 405 may be manufactured as a separate component 410 and be placed over housing 401 so as to cover opening 402.

Figure 5A:
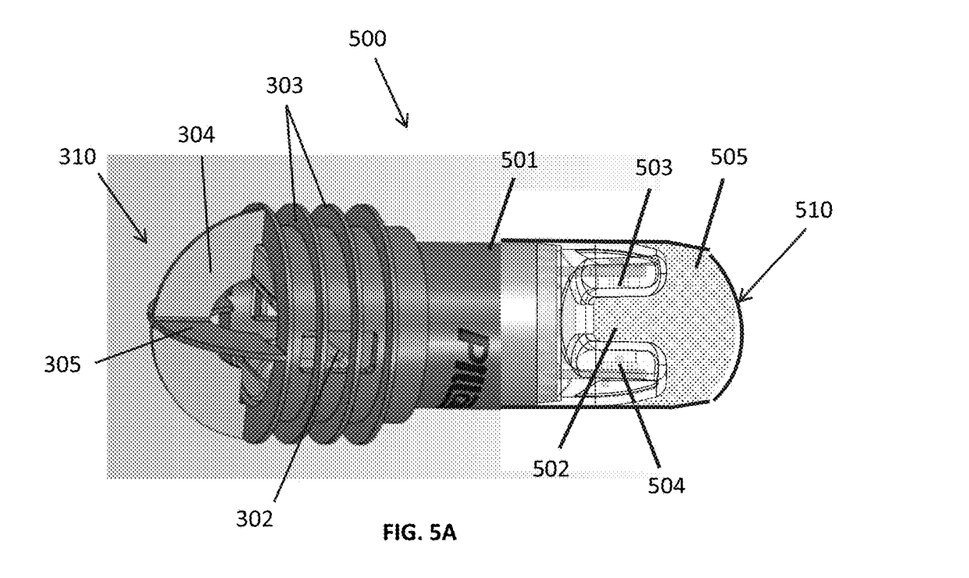
FIGS. 5A-5B are schematic illustrations of a side-view of an in-vivo device for the detection of blood within in-vivo fluids, and a side-view of a section of the in-vivo device, in accordance with a fourth embodiment of the present invention, respectively.
Figure 5B:
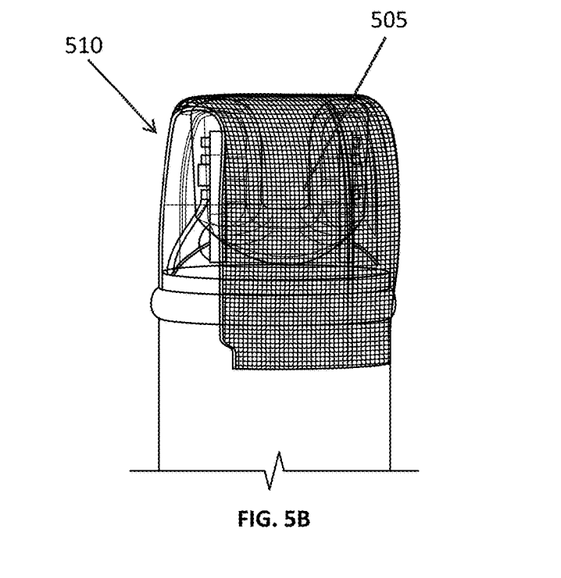

Reference is now made to FIGS. 5A-5B, which schematically illustrate a side-view of an in-vivo device for the detection of blood within in-vivo fluids, and a side-view of a section of the in-vivo device, in accordance with a fourth embodiment of the present invention, respectively. Device 500 may comprise housing, shell or case 501. Device 500 may be similar to device 100 such that it comprises an illumination source and a light detector located on opposite sides of a gap. In-vivo fluids may enter and/or exit the gap such to be examined for presence of blood by the readings of light that passes through the in-vivo fluids, which may be collected by the light detector. Housing 501 may comprise two sensing heads with different protective means on each of the sensing heads. First end 310 may be similar to the end of device 300. End 310 may comprise flexible fins 303, which may cover opening 302 when flexible fins 303 fold due to peristaltic pressure applied onto fins 303. End 310 may further comprise at least one all or partition 304 positioned on the top end of opening 302. In some embodiments, device 500 may further comprise partition 305 at end 310, in order to better ensure that tissue does not enter opening 302, which may disrupt readings acquired by the light detector. In other embodiments, any of the protective means illustrated in FIG. 2A and FIG. 4A may replace end 310.

Housing 501 may further comprise end 510, typically located opposite end 310. End 510 may be similar to end 310, since end 510 may also comprise an illumination source and a light detector on both sides of a gap. End 510 may comprise at least one illumination source 503 and at least one light detector 504, located on both sides of gap 502. However, end 510 may further comprise membrane 505 that may cover gap 502. Membrane 505 may also by a hydrogel cover.

In some embodiments, in order to avoid entry of GI content other than fluids into gap 502, thereby perhaps blocking it, gap 502 may include a membrane cover, or a hydrogel cover, across the mouth of gap 502. The membrane or hydrogel may cover the entire gap 502, and may have holes or pores that allow only particles of a certain size or smaller to pass through them. The size of the pores in the membrane or hydrogel may be designed to selectively allow passage of particles with a size similar to the size of blood particles flowing in in-vivo fluids. For example, the size of the pores may be similar to the sizes of globin A and globin B or of glycophorin A. However, particles larger than blood related particles may not enter through the designed holes of membrane 505.

End 310 of device 500 may be used to detect the presence of blood within in-vivo fluids along the upper GI tract and along the small bowel, where the lumen walls often contract due to peristaltic waves and may thus be pushed against housing 501. In order to prevent such tissue or mucosa from entering the sensing area in end 310 of housing 500, end 310 comprises the means for pushing the tissue away from opening 302 and thus away from the sensing area. The flexible fins 303 push the tissue away from opening 302, while allowing in-vivo fluids to enter and/or exit opening 302.

End 510 of device 500 may be used to detect presence of blood within in-vivo fluids along the large intestine or colon of a patient. Since the colon walls usually have a diameter that is larger than that of a typical swallowable capsule, tissue does not tend to be pushed against device 500. However, the colon is typically filled with turbid content (unless pre-cleaned with various known cleansing methods), which might enter device 500. Therefore, membrane 505 is designed to allow passage of particles of a certain size that is of interest for detecting presence of blood within in-vivo fluids. FIG. 5B illustrates the holes in membrane 505 in greater detail, as an example for a membrane that may be used to cover opening 502.

Device 500 may be a device that is suitable for detecting blood along the entire GI tract. End 310 is typically suitable for detecting blood within in-vivo fluids flowing within the upper GI tract and the small bowel, whereas end 510 is typically suitable for detecting presence of blood within in-vivo fluids flowing inside the colon.

Device 500 may be administered into the GI tract, e.g., by swallowing. In some embodiments, device 500 may be a swallowable capsule.

Figure 6:
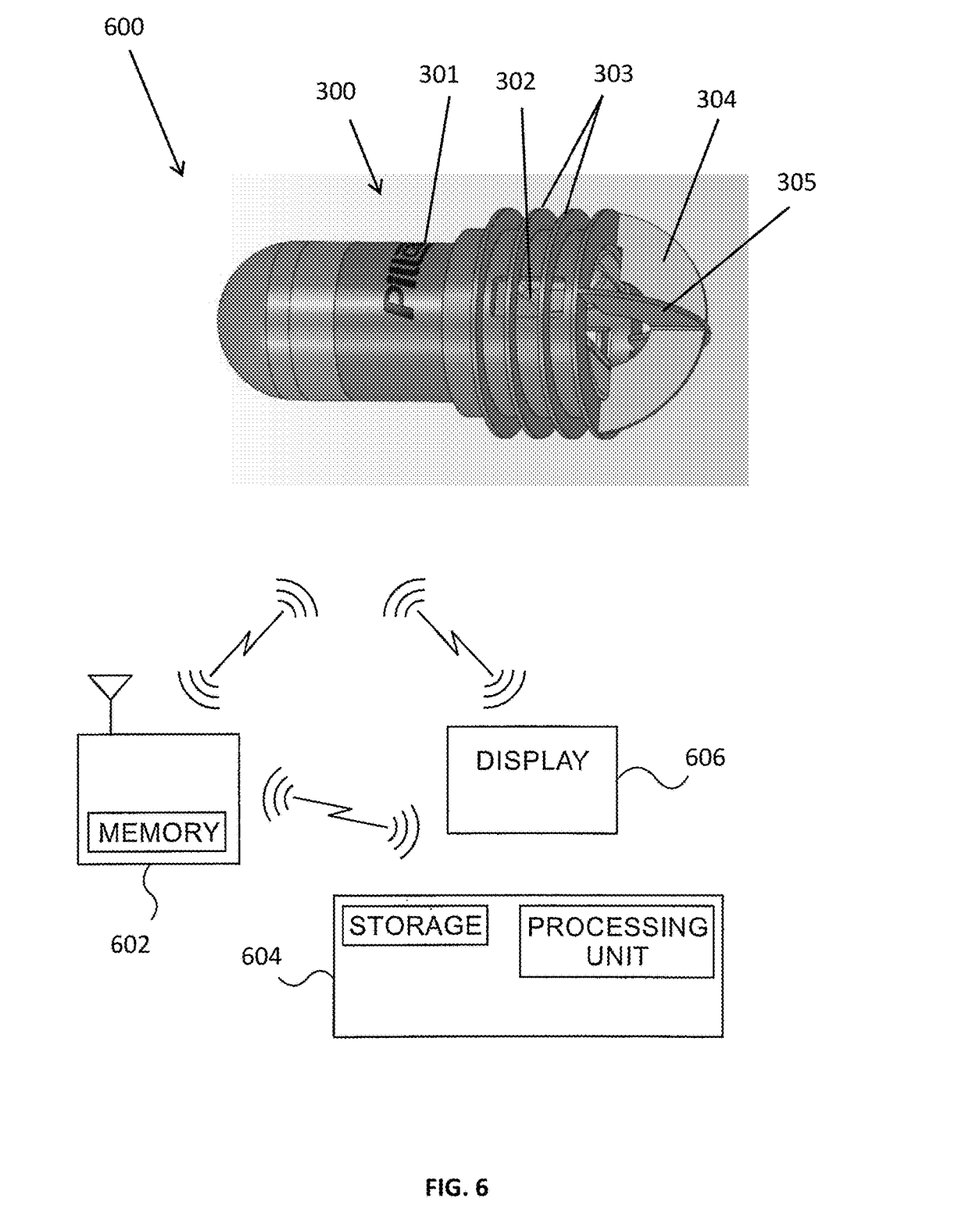
FIG. 6 is a schematic illustration of a system in accordance with one embodiment of the present invention.

Reference is now made to FIG. 6, which schematically illustrates a system in accordance with one embodiment of the present invention. System 600 may comprise an in-vivo sensing device for detection of blood within in-vivo fluids. The in-vivo device may be any of devices 200, 300, 400 or 500, as described in FIGS. 2, 3, 4 and 5, respectively. FIG. 6 illustrates device 300 as an example for an in-vivo sensing device used to detect presence of blood within in-vivo fluids of the GI tract. Device 300 may typically be administered to a patient by swallowing. However, other administration methods are possible, e.g., by an endoscope, by a capsule delivery device such as the one disclosed in U.S. Pat. Nos. 6,632,171 and 6,884,213, or by surgery. System 600 may further comprise a receiver 602, computing device 604, and display 606.

According to some embodiments of the invention, system 600 may comprise an in-vivo sensing device, e.g., device 300, that may transmit light signal and/or other information (e.g., images, pH values, etc.) to a data receiver and/or recorder 602 possibly close to or worn on a subject. In some embodiments, the in-vivo device, e.g., device 300 may comprise a transmitter (not shown) for transmitting the detected illumination that passed through the in-vivo fluids, to external receiver 602. Typically, the transmitter housed within device 300 is a wireless transmitter, e.g., transmitting signals in radio frequency (RF) transmission. Receiver 602 may comprise a memory unit for storing the data transmitted from device 300.

A data receiver and/or recorder 602 may of course take other suitable configurations. The data receiver and/or recorder 602 may transfer the received information to a larger computing device 604, such as a workstation or personal computer, where the data may be further analyzed, stored, and/or displayed to a user. In other embodiments, display 606 may be a separate unit not part of computing device 604. In other embodiments, each of the various components need not be required; for example, an internal device may transmit or otherwise transfer (e.g., by wire) information directly to a viewing or processing system.

In some embodiments, computing device 604 may comprise a processing unit and a storage unit. The processing unit may create a transmission spectrum from the light signals detected by the light detector, which correspond to the transmission spectra of the in-vivo fluids. The processing unit may then compare the created transmission spectra to reference transmission spectra of, e.g., bile. The processing unit may either compare the entire spectra or compare only a number of values in order to determine whether bile is present in the correlating locations in-vivo. Further processing may be done as described in FIG. 5 of International Patent Application Publication No. WO 2010/086859.

In some embodiments, display 606 may display the transmission spectra of the in-vivo fluids. In other embodiments, display 606 may display the transmission spectra along with other information, e.g., pH values at the correlating in-vivo locations of where the light signals were detected. In other embodiments, where device 300 may, for example, comprise an imager and a broad band illumination source, i.e., white light, in-vivo images may be displayed either alone or alongside the in-vivo locations where blood/bile or both were detected. Typically, the imager and broad band illumination source would be located on one end of the device's housing opposite the end comprising the illumination source, the gap and the light detector.

It will be appreciated that the present invention is not limited to what has been particularly shown and described hereinabove. Rather the scope of the present invention is defined only by the claims which follow.

The invention claimed is:

1. An in-vivo sensing device for detection of blood within in-vivo gastrointestinal fluids, said device comprising:
   a housing comprising:

a gap formed into or through said housing and having at least one opening through which in-vivo fluids may enter and/or exit the gap;
an illumination source for illuminating the in-vivo fluids in said gap;
a light detector for detecting light that passes through the in-vivo fluids in said gap; and
a flexible fin disposed on said housing adjacent to said opening, the flexible fin made from a material such that the flexible fin folds by peristaltic pressure applied to the flexible fin, and the flexible fin unfolds by the peristaltic pressure being released from the flexible fin, wherein the flexible fin is configured to cover said opening when the flexible fin is folded, and to allow free fluid flow of in-vivo fluids through said opening when the flexible fin is unfolded.

2. The in-vivo sensing device according to claim 1, wherein said flexible fin is circular such that the flexible fin surrounds the entire circumference of the housing.

3. The in-vivo sensing device according to claim 1, wherein said device further comprises:
a second gap through which in-vivo fluids may enter and exit;
an illumination within said second gap source for illuminating in-vivo fluids in said second gap;
a light detector within said second gap for detecting light that passes through the in-vivo fluids in said second gap; and
a membrane covering said second gap, wherein said membrane selectively enables passage of particles of a certain size into and/or out of the gap;
wherein said second gap, illumination source, light detector and membrane are located on one end of the device's housing, opposite the end comprising the opening covered by the flexible fin.

4. The in-vivo sensing device according to claim 1, wherein the flexible fin comprises a flexible material.

5. The in-vivo sensing device according to claim 1, wherein the flexible fin comprises an elastomer.

6. The in-vivo sensing device according to claim 1, wherein the flexible fin is external to said opening.

7. An in-vivo sensing system for detection of blood within in-vivo gastrointestinal fluids, said system comprising:
an in-vivo sensing device comprising a housing, said housing comprising:
a gap formed into or through said housing, the gap having at least one opening through which in-vivo fluids may enter and/or exit the gap;
an illumination source for illuminating the in-vivo fluids in said gap;
a light detector for detecting light that passes through the in-vivo fluids in said gap;
a flexible fin disposed on said housing in the vicinity of said opening, the flexible fin made from a material such that the flexible fin folds by peristaltic pressure applied to the flexible fin, and the flexible fin unfolds by the peristaltic pressure being released from the flexible fin, wherein the flexible fin and configured to cover said opening when the flexible fin is folded, and to allow free fluid flow of in-vivo fluids through said opening when the flexible fin is in unfolded; and
a transmitter for transmitting signals detected by said light detector; and
a receiver for receiving the detected signals; and
a processing unit for processing the detected signals to determine presence of blood in-vivo.

8. The system according to claim 7 further comprising:
a second illumination source for providing broad band illumination; and
an imager for acquiring in-vivo images,
wherein said second illumination source and said imager are positioned on one end of the device's housing opposite the end comprising the illumination source, the gap and the light detector.

9. The system according to claim 7, wherein said in-vivo device is a swallowable capsule.

* * * * *